US008673623B2

(12) United States Patent
Davey

(10) Patent No.: US 8,673,623 B2
(45) Date of Patent: Mar. 18, 2014

(54) APPARATUS FOR PERFORMING MAGNETIC ELECTROPORATION

(75) Inventor: Kent Davey, Austin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 129 days.

(21) Appl. No.: 12/198,443

(22) Filed: Aug. 26, 2008

(65) Prior Publication Data

US 2009/0061504 A1 Mar. 5, 2009

Related U.S. Application Data

(60) Provisional application No. 60/969,183, filed on Aug. 31, 2007.

(51) Int. Cl.
*C12M 1/42* (2006.01)
*C12M 3/00* (2006.01)
*C12N 3/00* (2006.01)

(52) U.S. Cl.
CPC . *C12M 35/02* (2013.01); *C12N 3/00* (2013.01)
USPC ...... 435/285.2; 435/470; 435/461; 435/173.6

(58) Field of Classification Search
CPC ...... C12M 35/02; C12M 23/12; C12M 35/04; C12N 13/00; C12N 15/87; C12N 15/8207; C12N 15/8206; H03K 3/57; G01N 33/48728; A61N 1/306
USPC ............................ 435/173.6, 285.2, 461, 470
See application file for complete search history.

(56) References Cited

U.S. PATENT DOCUMENTS

| | | | | |
|---|---|---|---|---|
| 3,213,520 | A | 10/1965 | Vaughan | |
| 3,229,124 | A | 1/1966 | Schoffield | |
| 3,845,322 | A | 10/1974 | Aslin | |
| 4,363,088 | A | 12/1982 | Yamamoto et al. | |
| 4,432,873 | A * | 2/1984 | Schuster | 210/223 |
| 4,695,472 | A | 9/1987 | Dunn et al. | |
| 4,946,793 | A | 8/1990 | Marshall, III | |

(Continued)

FOREIGN PATENT DOCUMENTS

| | | |
|---|---|---|
| DE | 455933 | 2/1928 |
| EP | 1501176 A2 | 1/2005 |

(Continued)

OTHER PUBLICATIONS

Definition of coaxial (www.meriam-webster.com/dictionary/co-axial; printed on Nov. 2, 2010).*

(Continued)

*Primary Examiner* — Michael Hobbs
(74) *Attorney, Agent, or Firm* — Daniel J. Chalker; Edwin S. Flores; Chalker Flores, LLP

(57) ABSTRACT

An apparatus for performing magnetic electroporation is disclosed. A required electric field for electroporation is generated using a pulsed magnetic field through a closed magnetic yoke, such as a toroid, placed in a flow path of a fluid medium to be processed. The fluid medium flows through the orifice of the magnetic yoke, with the fluid medium flowing through and around the yoke. The required power to send a maximum flux through the magnetic yoke is less than the required power in a conventional apparatus for performing electroporation.

20 Claims, 2 Drawing Sheets

(56) References Cited

U.S. PATENT DOCUMENTS

| | | | | |
|---|---|---|---|---|
| 5,690,978 | A | 11/1997 | Yin et al. | |
| 5,776,529 | A | 7/1998 | Qin et al. | |
| 6,010,613 | A | 1/2000 | Walters et al. | |
| 6,043,066 | A | 3/2000 | Magano et al. | |
| 6,214,297 | B1 | 4/2001 | Zhang et al. | |
| 6,258,592 | B1 | 7/2001 | Ragsdale et al. | |
| 6,326,177 | B1 | 12/2001 | Schoenbach et al. | |
| 6,491,820 | B2 | 12/2002 | Held et al. | |
| 6,653,114 | B2 | 11/2003 | Walters et al. | |
| 6,654,640 | B2 | 11/2003 | Lyden | |
| 6,673,597 | B2 | 1/2004 | Wolf et al. | |
| 6,768,621 | B2 | 7/2004 | Arnet et al. | |
| 6,771,518 | B2 | 8/2004 | Orr et al. | |
| 6,783,647 | B2 | 8/2004 | Culbertson et al. | |
| 6,900,557 | B1 | 5/2005 | Gaudreau et al. | |
| 7,186,559 | B2 | 3/2007 | Dzekunov et al. | |
| 7,497,119 | B2 | 3/2009 | Brooks et al. | |
| 7,507,341 | B2 | 3/2009 | Gallagher et al. | |
| 7,662,616 | B2 | 2/2010 | Hazlebeck et al. | |
| 7,691,324 | B2 | 4/2010 | Shultheiss | |
| 7,767,433 | B2 | 8/2010 | Kuthi et al. | |
| 7,902,695 | B2 | 3/2011 | London | |
| 8,017,367 | B2 | 9/2011 | Vassanelli et al. | |
| 8,048,067 | B2 | 11/2011 | Davalos et al. | |
| 8,088,614 | B2 | 1/2012 | Vick et al. | |
| 2002/0103515 | A1* | 8/2002 | Davey et al. | 607/66 |
| 2003/0006706 | A1 | 1/2003 | Yamaguchi et al. | |
| 2003/0170898 | A1 | 9/2003 | Gunderson et al. | |
| 2004/0084381 | A1* | 5/2004 | Korenev | 210/748 |
| 2004/0115758 | A1 | 6/2004 | Shimada et al. | |
| 2004/0165408 | A1 | 8/2004 | West et al. | |
| 2004/0197883 | A1* | 10/2004 | Dzekunov et al. | 435/173.6 |
| 2005/0026202 | A1 | 2/2005 | Edman et al. | |
| 2005/0030772 | A1 | 2/2005 | Phadke | |
| 2005/0098430 | A1 | 5/2005 | Tuymer et al. | |
| 2006/0245217 | A1 | 11/2006 | Kirbie et al. | |
| 2007/0025124 | A1 | 2/2007 | Hansson et al. | |
| 2007/0043345 | A1 | 2/2007 | Davalos et al. | |
| 2007/0207528 | A1 | 9/2007 | Picataggio et al. | |
| 2008/0215032 | A1 | 9/2008 | Rabussay | |
| 2008/0220491 | A1 | 9/2008 | Zimmermann et al. | |
| 2009/0035856 | A1 | 2/2009 | Galliher et al. | |
| 2009/0061504 | A1 | 3/2009 | Davey | |
| 2009/0087900 | A1 | 4/2009 | Davey et al. | |
| 2011/0065161 | A1 | 3/2011 | Kwasinski et al. | |
| 2011/0107655 | A1 | 5/2011 | Kempkes et al. | |
| 2012/0021481 | A1 | 1/2012 | Hebner | |
| 2012/0252087 | A1 | 10/2012 | Hebner | |

FOREIGN PATENT DOCUMENTS

| | | | |
|---|---|---|---|
| WO | 03064590 | A2 | 8/2003 |
| WO | 2006004558 | A1 | 1/2006 |
| WO | 2008098298 | A1 | 8/2008 |
| WO | 2009042501 | A1 | 4/2009 |
| WO | 2010045631 | A2 | 4/2010 |
| WO | 2010104922 | A1 | 9/2010 |
| WO | 2010115875 | A1 | 10/2010 |
| WO | 2010123903 | A1 | 10/2010 |
| WO | 2011032149 | A2 | 3/2011 |
| WO | 2011056223 | A1 | 5/2011 |
| WO | 2011133181 | A1 | 10/2011 |
| WO | 2012010969 | A1 | 1/2012 |
| WO | 2012138741 | A2 | 10/2012 |

OTHER PUBLICATIONS

Baek, et al. "Solid State Marx Generator Using Series-Connected IGBTs" IEEE 0-7803-8586-1/04 copyright 2004.

Beverige, et al. "The Influence of pulse duration on the inactivation of bacteria using monopolar and bipolar profile pulsed electric fields" IEEE Transactions on Plasma Science. Aug. 2005 33(4): 1287-1293.

Heger, et al. "A new processing scheme for algae biofuels" MIT Technology Review [online], May 1, 2009 [retrieved on Aug. 27, 2013] retrieved from the internet: <URL: http://www.technologyreview.com/news/413325/a-new-processing-scheme-for-algae-biofuels/#print>. 2 pp.

IEEE 100: The Authoritative Dictionary of IEEE Standards Terms, 7th edition. New York: IEEE Press, 2000, pp. 417 and 987.

Kempkes, et al. "Scaleup of PEF Systems for Food and Waste Streams" IEEE 1-4244-0914-4/07 Copyright 2007.

Redondo, et al. "Repetitive High-Voltage Solid-State Marx Modulator Design for Various Load Conditions" IEEE Transactions on Plasma Science, vol. 37, No. 8, pp. 1632-1637, Aug. 2009.

Reichle, et al. "A new microsystem for automated electrorotation measurements using laser tweezers" Biochimica et Biophysica Acta. 2000. 1459:218-229.

Sanchis, et al. "Dielectric characterization of bacterial cells using dielectrophoresis" Bioelectromagnetics. 2007. 28:393-401.

Wu, et al. "Analysis and a Design of a Soft-Switching Interleaved Forward Converter for Generating Pulsed Electric Fields" IEICE/IEEE INTELEC '03, Oct. 19-23, 2003.

Angersbach, et al. "Effects of pulsed electric fields on cell membranes in real food systems," Innovative Food Science and Emerging Technologies, vol. 1, No. 2, pp. 135-149(15), Jun. 2000.

Bae, et al. "High-Power Pulse Generator with Flexible Output Pattern" IEEE Transations on Power Electronics, vol. 25, No. 7, Jul. 2010, pp. 1675-1684.

Baek, et al. "Solid State Marx Generator Using Series-Connected IGBTs" IEEE Transactions on Plasma Science, vol. 33, pp. 1198-1204, Aug. 2005.

Bai-Lin, et al. "Inactivation of Microorganisms by Pulsed Electric Fields of different voltage waveforms," Dielectrics and Electrical Insulation, IEEE Transactions on, vol. 1, pp. 1047-1057, 1994.

Behrend, et al. "Pulse Generators for Pulsed Electric Field Exposure of Biological Cells and Tissues", IEEE Transactions on Dielectrics and Electrical Insulation, 2003, vol. 10; PART 5, pp. 820-825.

Canacsinh, et al. "New Solid-State Marx Topology for Bipolar Repetitive High-Voltage Pulses," Power Electronics Specialists Conference, 2008. PESC 2008. IEEE, 2008, pp. 791-795.

Chang, Donald C., "Cell Poration and Cell Fusion Using an Oscillating Electric Field," Biophysical Journal, vol. 56, Issue 4, pp. 641-652, Oct. 1989.

Eltron Research & Development Tech Brief, "Electroporation of Algae Cells" www.eltronresearch.com, Nov. 2009, 1 pg.

2nd Written Opinion of the International Preliminary Examining Authority for PCT/IB2011/002211 dated Jun. 25, 2012.

Ghasemi, et al., "Development of an integrated solid-state generator for light inactivation of food-related pathogenic bacteria", Institute of Physics Measurement Science and Technology, 2003, vol. 14, PART 6, pp. N26-N32.

Grenier, et al. "MOSFET-Based Pulse Power Supply for Bacterial Transformation", IEEE Transactions on Industry Applications, 2008, vol. 44; No. 1, pp. 25-31.

Heeren, et. al. "Novel Dual Marx Generator for Microplasma Applications," EEE Transactions on Plasma Science, vol. 33, No. 4, pp. 1205-1209, Aug. 2005.

Zimmerman, et al. "The Effect of Pressure on the Electrical Breakdown in the Membranes of Valonia Utricularis" Biochimica et. Biophysica Acta, vol. 464, pp. 399-416, 1977.

United States Patent & Trademark Office (International Searching Authority), International Search Report and Written Opinion for PCT/US2010/002899 dated Jan. 11, 2011.

Korean Intelectual Property Office (International Searching Authority), International Search Report and Written Opinion for PCT/US2010/048781 dated May 26, 2011, 11 pp.

Australian Patent Office (International Searching Authority), International Preliminary Report on Patentability for PCT/IB2011/002211 dated Sep. 17, 2012.

Australian Patent Office (International Searching Authority), International Search Report and Written Opinion for PCT/IB2011/002211 dated Feb. 8, 2012.

United States Patent & Trademark Office (International Searching Authority), International Search Report and Written Opinion for PCT/US2008/076926 dated Dec. 5, 2008.

(56) References Cited

OTHER PUBLICATIONS

Korean Intelectual Property Office (International Searching Authority), International Search Report and Written Opinion for PCT/US2012/032145 dated Sep. 27, 2012, 8 pp.
Keith, et al. "Pulsed electric fields as a processing alternative for microbial reduction in spice," Food Research International, vol. 30, pp. 185-191, May 1997.
Kim, et al. "A high-voltage bi-polar pulse generator a using push-pull inverter", Proc. Industrial Electronics Society Conference, 2003, vol. 1, pp. 102-107.
Kim, J.H., et al., "Semiconductor switch-based fast high-voltage pulse generators," Pulsed Power Conference, 2003. Digest of Technical Papers. PPC-2003. 14th IEEE International, 2003, pp. 665-668, vol. 1.
Kim, et al. "High Voltage Pulse Power Supply Using Marx Generator & Solid-State Switches" Industrial Electronics Society, 2005. pp. 1244-1124.
Kim, et al. "High Voltage Marx Generator Implementation using IGBT Stacks" IEEE Transactions on Dielectrics and Electrical Insulation, vol. 14, No. 4; pp. 931-936, Aug. 2007.
Kolb, et al. "Nanosecond pulsed electric field generators for the study of subcellular effects", Bioelectromagnetics, 2006, vol. 27, No. 3, pp. 172-187.
Kotnik, et. al. "Cell membrane electropermeabilization by symmetrical bipolar rectangular pulses: Part I. Increased efficiency of permeabilization" Bioelectrochemistry, vol. 54, issue 1, pp. 83-90, Aug. 2001.
Li, et al. "Development of Rectangle-Pulse Marx Generator Based on PFN" IEEE Transactions on Plasma Science, vol. 37, No. 1, pp. 190-194, Jan. 2009.
Liu, et al. "Nickel-inducible lysis system in *Synechocystis* sp. PCC 6803" PNAS, vol. 106, No. 51, Dec. 22, 2009, pp. 21550-21554.
New Energy and Fuel "Poking Holes in Corn for Ethanol" Feb. 12, 2009, http://newenergyandfuel.com/http:/newenergyandfuel/com/2009/02/12/poking-holes-in-corn-for-ethanol/.
Petkovsek, et al., "Multilevel bipolar high voltage pulse source—interlock dead time reduction", EUROCON 2003, vol. 2, pp. 240-243.
Puc, Marko, et al., "Techniques of Signal Generation Required for Electropermeabilization. Survey of Electropermeabilzation Devices," Bionergetics, vol. 41, Issue 2, pp. 135-160, Dec. 1996.
Redondo, et al., "Generalized Solid-state Marx 5 Modulator Topology", IEEE Transactions on Dielectrics and Electrical Insulation, Aug. 2009, vol. 16, No. 4.
Redondo, et. al. "Solid-state Marx Generator Design with an Energy Recovery Reset Circuit for Output Transformer Association" Rec. PESC 2007, pp. 2987-2991.
Redondo, et al. "Generalized Solid-state Marx Modulator Topology" IEEE Transactions on Dielectrics and Electrical Insulation, vol. 16, pp. 1037-1042, Aug. 2009.
Wu, et. al. "Repetitive and High Voltage Marx Generator Using Solid-state Devices" IEEE Transactions on Dielectrics and Electrical Insulation, vol. 14, No. 4, pp. 937-940, Aug. 2007.
Sanders, et al., "A Linear, Singlestage, Nanosecond Pulse Generator for Delivering Intense Electric Fileds to Bilogical Loads", IEEE Transactions on Dielectrics and Electrical Insulation, Aug. 2009, vol. 16, No. 3.
Zimmerman, et al., "Dielectric Breakdown of Cell Membranes," Biophysical Journal, vol. 14, pp. 881-899, 1974.
Sack, et al. "Upgrade of the Electroporation Device KEA-MOBIL" Proceedings of the 2nd Euro-Asian Pulsed Power Conference, Vilnius, Lithuania, Sep. 22-26, 2008, vol. 115 (2009), No. 6, pp. 1081-1083.
Singer, S. "Transformer description of a family of switched systems" IEE Proceedings of Electronic Circuits and Systems, vol. 129, issue 5, pp. 205-210, Oct. 1982.
Tekle, E., et al., "Electroporation by Using Bipolar Oscillating Electric Field: An Improved Method for DNA Transfection of NIH 373 Cells," Proc. National Academy of Science, vol. 88, pp. 4230-4234, May 1991.
Topfl, Stefan, Pulsed Electric Fields (PEF) for Permeabilization of Cell Membranes in Food- and Bioprocessing—applications, Process and Equipment Design and Cost Analysis, Ph.D. Dissertation, Berlin University of Technology, Berlin, Germany, Sep. 2006.
Tsong, Tian Y., "Electroportion of Cell Membranes," Biophysical Journal: 60(2): pp. 297-306, Aug. 1991.
Weaver, et al. "Theory of electroporation: A review" Bioelectrochemistry and Bionergetics, vol. 41, issue 2, pp. 135-160, Dec. 1996.
Wikipedia, the free encyclopedia, May 10, 2011 "Pulsed Elecrtic Field Processing".

* cited by examiner

APPARATUS FOR PERFORMING MAGNETIC ELECTROPORATION

PRIORITY CLAIM

The present application claims priority under 35 U.S.C. §119(e)(1) to provisional application No. 60/969,183 filed on Aug. 31, 2007, the contents of which are incorporated herein by reference.

BACKGROUND OF THE INVENTION

1. Technical Field

The present invention relates to electroporation in general, and, in particular, to an apparatus for performing magnetic electroporation.

2. Description of Related Art

In general, electroporation is a process by which a biological cell is exposed to a high-voltage electric potential to generate transitory pores in the cell membrane that reclose after the electric potential is removed. The sizes of transitory pores allow large molecules, such as nucleic acids and proteins, to enter a cell from a medium in which the cell is stored.

As a means of infusing biological cells with various types of molecules, electroporation is particularly useful in placing inside living cells deoxyribonucleic acid (DNA) that is foreign to the living cells, thereby enabling the living cells to express desirable proteins or to otherwise behave in a specified manner dictated by the infused DNA. Electroporation has also been used extensively in transferring drugs to the interior of a living cell. In addition, electroporation can be used to kill bacteria and yeast, such as in the fermentation process of grapes to make wine.

An electroporation apparatus typically includes a cuvette to hold a cell suspension and a shocking chamber in which the cuvette is inserted. The amount of voltage used in electroporation depends on the cell type and the species being infused. Smaller cells, for example, tend to require higher field strengths, as do larger molecules. Thus, voltages used in electroporation can range from as low as 200 V/cm to as high as 35,000 V/cm. With voltages of such high magnitude, user safety becomes a huge concern.

The present disclosure provides an improved apparatus for performing electroporation.

SUMMARY OF THE INVENTION

In accordance with a preferred embodiment of the present invention, a ferrous toroid fit within an insulating sleeve is placed within a fluid medium in which the fluid medium flows through an annulus of the ferrous toroid. An electric current is circulated around the ferrous toroid such that an electric field is induced by the changing magnetic field. The electric field has a closed path within the fluid medium.

All features and advantages of the present invention will become apparent in the following detailed written description.

BRIEF DESCRIPTION OF THE DRAWINGS

The invention itself, as well as a preferred mode of use, further objects, and advantages thereof, will best be understood by reference to the following detailed description of an illustrative embodiment when read in conjunction with the accompanying drawings, wherein.

DETAILED DESCRIPTION OF A PREFERRED EMBODIMENT

Figure 1:
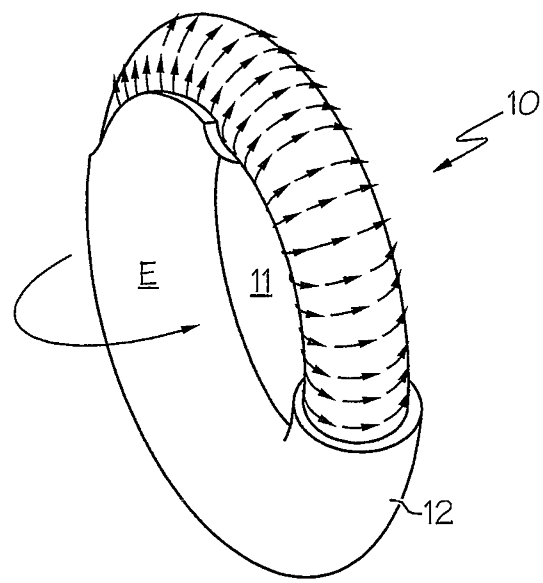
FIG. 1 is a diagram of a magnetic toroid to be utilized for performing magnetic electroporation, in accordance with a preferred embodiment of the present invention.

Referring now to the drawings and in particular to FIG. 1, there is depicted a diagram of a magnetic toroid to be utilized for performing magnetic electroporation, in accordance with a preferred embodiment of the present invention. As shown, a toroid 10 made of a ferrous medium is fit within an insulating sleeve 12. Toroid 10 can be placed within a fluid medium in which the fluid medium flows through an annulus 11 and around toroid 10. During operation, electric current circulates around toroid 10 to excite toroid 10, and when the magnitude of the electric current changes, the magnetic field within toroid 10 induces an electric field that has a closed path within the fluid medium. The electric field concentrates in annulus 11. The electric field anywhere through annulus 11 is sufficient to achieve sustained electroporation for any material passing through annulus 11.

Multiple toroids 10 can be placed in parallel to increase electroporation throughput and to provide a closed ion current path without the requirement of the fluid medium flowing around toroids 10. For example, in applications involving the destruction of bacteria and yeast, multiple toroids 10 can be placed in series to increase the destruction ratio.

Figure 2:
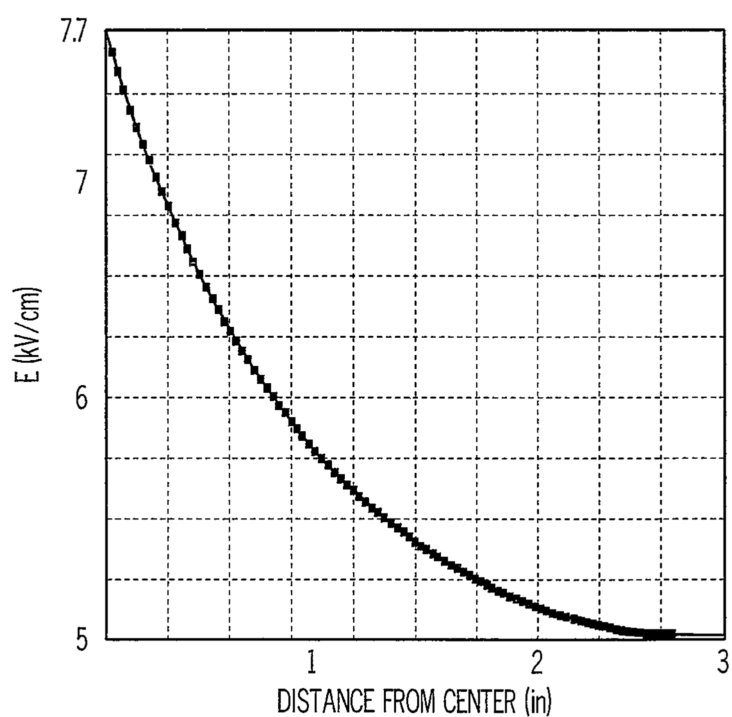
FIG. 2 graphically illustrates an induced electric field for the magnetic toroid of FIG. 1.

With reference now to FIG. 2, there is graphically illustrated an induced electric field for toroid 10. For the present example, toroid 10 has a cross-sectional diameter of 2" with a 6" diameter annulus 11. Toroid 10 is excited by electric current at 10 MHz, and an induced electric field is plotted along the radius of annulus 11. As shown, the magnitude of electric field generated by toroid 10 is highest at the center of annulus 11 and decreases exponentially towards the edge of toroid 10.

The power to excite toroid 10 is proportional to the current flow in the fluid medium, which has a conductivity of 0.15 S/m. The advantage presented is the ability to concentrate electroporation within the center of annulus 11, and completely avoid all half cell reaction. Toroid 10 can be excited with capacitors, with the capacitors being charged in parallel and discharged in series. The capacitance of the series combination drops, making for a small $1/\sqrt{LC}$ resonant frequency.

Figure 3:
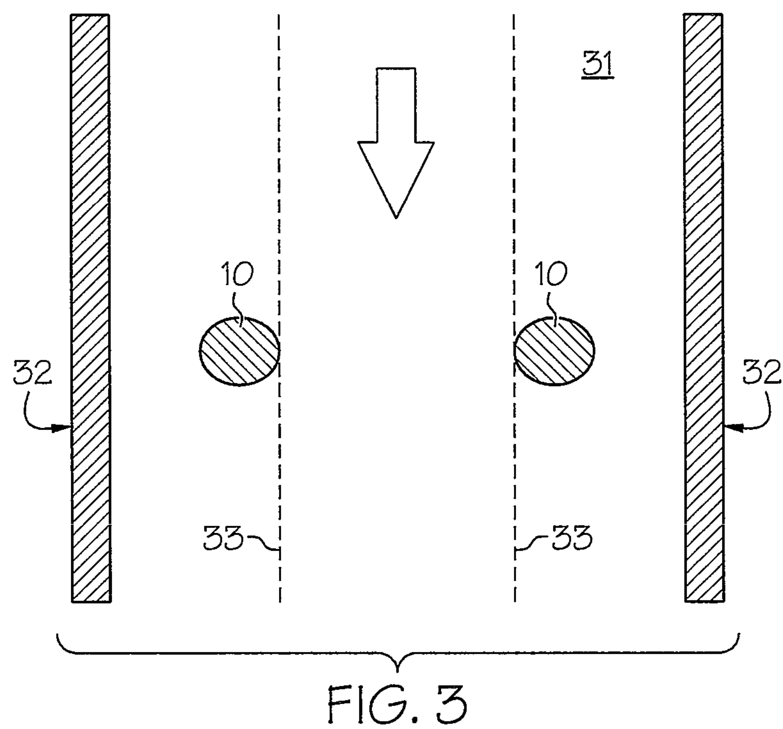
FIG. 3 is a diagram of an apparatus for performing magnetic electroporation, in accordance with a preferred embodiment of the present invention.

Referring now to FIG. 3, there is depicted a diagram of an apparatus for performing magnetic electroporation, in accordance with a preferred embodiment of the present invention. As shown, a toroid, such as toroid 10 from FIG. 1, is placed within a fluid medium 31 contained within a pipe 32. Materials to be processed, such as sugar beets and grapes, are forced through annulus 11 of toroid 10 by the use of a screen 33. Even if screen 33 becomes fouled, screen 33 does not impede the flow of ions induced during the discharge. However, screen 33 does not work in decontamination applications.

Figure 4:
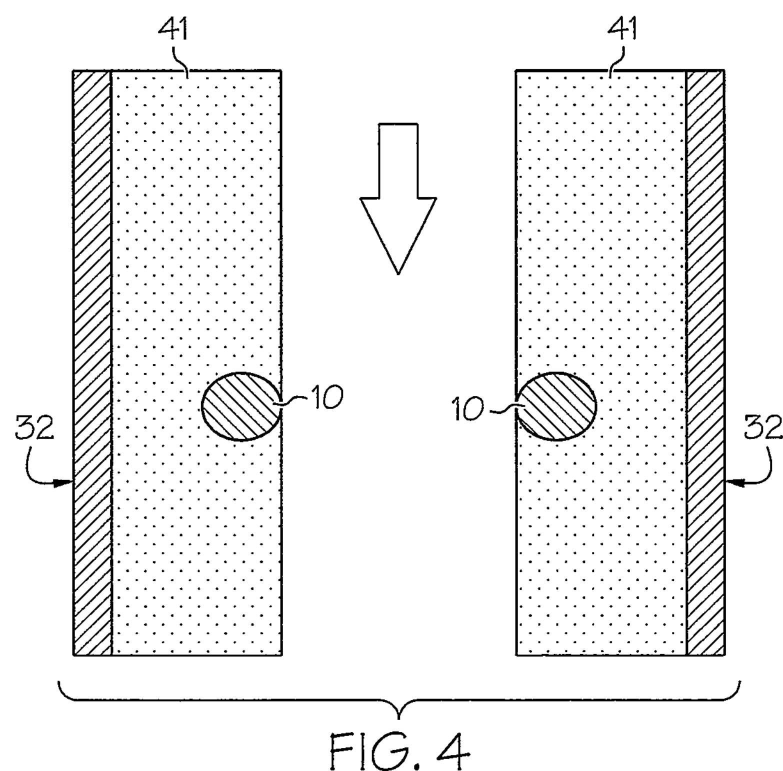
FIG. 4 is a diagram of an apparatus for performing magnetic electroporation in decontamination applications, in accordance with a preferred embodiment of the present invention.

With reference now to FIG. 4, there is depicted a diagram of an apparatus for performing magnetic electroporation in decontamination applications, in accordance with a preferred embodiment of the present invention. As shown, an agar gel 41 (instead of screen 33) is placed within a fluid medium to serve as a solid barrier, one that allows ion flow. A toroid, such as toroid 10 from FIG. 1, having a 4" diameter and 1.5" from the edge of the toroid to an axis of rotation is suitable for this task. Am amp-turn product of 1,500 A at 4.5 MHz is necessary to induce an electric field of 5 kV/cm.

As has been described, the present invention provides an apparatus for performing magnetic electroporation. The present invention overcomes the disadvantages of the prior art apparatus by eliminating electrodes. Furthermore, a lower power requirement can be achieved by using a time changing magnetic field to induce an electric field. The two major factors for reducing power requirement are the employment of a closed magnetic yoke and the allowance of fluid medium to fully surround the yoke. In addition to power utilization, magnetic electroporation has the advantage of a functional volume that acts like a funnel of assurance.

While the invention has been particularly shown and described with reference to a preferred embodiment, it will be understood by those skilled in the art that various changes in form and detail may be made therein without departing from the spirit and scope of the invention.

What is claimed is:

1. An apparatus for performing magnetic electroporation, said apparatus comprising:

- a chamber through which a fluid medium flows;
- a ferrous toroid placed within said chamber and said fluid medium such that said fluid medium flows through an annulus of said ferrous torrid and around said ferrous toroid; and
- capacitors that circulate current around said ferrous toroid such that an electric field is induced by a magnetic field of said ferrous toroid when said circulating current changes within said ferrous toroid, wherein said electrical field has a closed path within said fluid medium around said ferrous toroid within said fluid medium and induces electroporation in said fluid medium flowing through said annulus of said ferrous toroid.

2. The apparatus of claim 1, wherein said ferrous toroid is placed within said fluid medium to allow ions to flow completely around said ferrous toroid within said fluid medium while forcing cells to be processed through said annulus of said ferrous toroid.

3. The apparatus of claim 1, wherein said ferrous toroid is contained within an insulating sleeve.

4. The apparatus of claim 1, wherein said chamber comprises a pipe.

5. The apparatus of claim 4, further comprising a screen coaxially aligned with and passing through said annulus of said ferrous toroid.

6. The apparatus of claim 1, wherein said ferrous toroid is contained within an agar gel that serves as a barrier to said fluid medium forcing said fluid medium through said annulus of said ferrous toroid while allowing ion flow around said ferrous toroid when performing decontamination applications.

7. The apparatus of claim 1, wherein said capacitors are capable of being charged in parallel and discharged in series.

8. The apparatus of claim 1, wherein said ferrous toroid is excited by a power proportional to a current flow in said fluid medium.

9. An apparatus for performing magnetic electroporation, said apparatus comprising:

- a pipe;
- a ferrous toroid disposed within, coaxially aligned with and separated from an inner wall of said pipe such that a fluid medium flows through an annulus of said ferrous toroid and around said ferrous toroid; and
- wherein an electric field is induced by a magnetic field of said ferrous toroid when a circulating current is changed within said ferrous toroid, and wherein said electrical field has a closed path within said fluid medium and induces electroporation in said fluid medium flowing through said annulus of said ferrous toroid.

10. The apparatus of claim 9, wherein said ferrous toroid is placed within said fluid medium to allow ions to flow completely around said ferrous toroid while forcing cells to be processed through said annulus of said ferrous toroid.

11. The apparatus of claim 9, wherein said ferrous toroid is contained within an insulating sleeve.

12. The apparatus of claim 9, further comprising an ion permeable barrier disposed within said pipe and coaxially aligned with said annulus of said ferrous toroid.

13. The apparatus of claim 12, wherein said ion permeable barrier comprises a screen.

14. The apparatus of claim 12, wherein said ion permeable barrier comprises an agar gel that extends to said inner wall of said pipe and directs said fluid medium through said annulus of said ferrous toroid.

15. The apparatus of claim 9, further comprising one or more capacitors electrically connected to said ferrous toroid wherein said circulating current is created by charging said capacitors in parallel and discharged said capacitors in series.

16. The apparatus of claim 9, wherein said ferrous toroid is excited by a power proportional to a current flow in said fluid medium.

17. An apparatus for performing magnetic electroporation, said apparatus comprising:

- a pipe;
- a ferrous toroid disposed within, coaxially aligned with and separated from an inner wall of said pipe such that a fluid medium flows through an annulus of said ferrous toroid and around said ferrous toroid;
- an insulating sleeve encapsulating said ferrous toroid;
- an ion permeable barrier disposed within said pipe and coaxially aligned with said annulus of said ferrous toroid to allow ions to flow completely around said ferrous toroid; and
- wherein an electric field is induced by a magnetic field of said ferrous toroid when a circulating current is changed within said ferrous toroid, and wherein said electrical field has a closed path within said fluid medium and induces electroporation in said fluid medium flowing through said annulus of said ferrous toroid.

18. The apparatus of claim 17, wherein said ion permeable barrier comprises a screen, or an agar gel that extends to said inner wall of said pipe and directs said fluid medium through said annulus of said ferrous toroid.

19. The apparatus of claim 17, further comprising one or more capacitors electrically connected to said ferrous toroid wherein said circulating current is created by charging said capacitors in parallel and discharged said capacitors in series.

20. The apparatus of claim 17, wherein said ferrous toroid is excited by a power proportional to a current flow in said fluid medium.

* * * * *